United States Patent
Tanaka et al.

(10) Patent No.: US 10,031,023 B2
(45) Date of Patent: Jul. 24, 2018

(54) SPECKLE IMAGING DEVICE, SPECKLE IMAGING SYSTEM, AND SPECKLE IMAGING METHOD

(71) Applicant: SONY CORPORATION, Tokyo (JP)

(72) Inventors: Eiichi Tanaka, Kanagawa (JP); Yusaku Nakashima, Tokyo (JP); Isamu Nakao, Tokyo (JP); Noriyuki Kishii, Kanagawa (JP); Takuya Kishimoto, Kanagawa (JP)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 15/547,303

(22) PCT Filed: Jan. 14, 2016

(86) PCT No.: PCT/JP2016/050910
§ 371 (c)(1),
(2) Date: Jul. 28, 2017

(87) PCT Pub. No.: WO2016/132778
PCT Pub. Date: Aug. 25, 2016

(65) Prior Publication Data
US 2018/0003557 A1 Jan. 4, 2018

(30) Foreign Application Priority Data
Feb. 18, 2015 (JP) ................. 2015-029951

(51) Int. Cl.
*G01J 3/44* (2006.01)
*G01J 3/02* (2006.01)
*G01N 21/47* (2006.01)

(52) U.S. Cl.
CPC ............ *G01J 3/02* (2013.01); *G01N 21/4788* (2013.01); *G01N 2021/479* (2013.01)

(58) Field of Classification Search
CPC ...... G01J 3/02; G01J 3/44; G01J 3/14; G01N 21/65; G01N 21/47; G01N 2021/65; G06F 3/04; G06K 9/20; G06K 9/62; G06T 7/20
See application file for complete search history.

(56) References Cited

U.S. PATENT DOCUMENTS

2007/0083114 A1* 4/2007 Yang ..................... A61B 8/00
600/437

FOREIGN PATENT DOCUMENTS

JP 2005-515818 A 6/2005
JP 2006-522341 A 9/2006
(Continued)

OTHER PUBLICATIONS

International Search Report and Written Opinion of PCT Application No. PCT/JP2016/050910, dated Mar. 15, 2016, 01 pages of English Translation and 05 pages of ISRWO.

*Primary Examiner* — Abdullahi Nur
(74) *Attorney, Agent, or Firm* — Chip Law Group

(57) ABSTRACT

Provided is a highly accurate imaging technology that utilizes the speckle interference. The present technology provides a speckle imaging device including: an irradiation condition setting unit that sets an irradiation condition for coherent light with which an imaging object is irradiated; an imaging unit that captures scattered light obtained from the imaging object irradiated with the coherent light; an image generation unit that generates a speckle-enhanced image from a captured image captured by the imaging unit; and a leveling processing unit that generates a leveled speckle image from speckle-enhanced images corresponding to two or more different irradiation conditions.

13 Claims, 5 Drawing Sheets

(56) References Cited

FOREIGN PATENT DOCUMENTS

| | | |
|---|---|---|
| JP | 2008-043493 A | 2/2008 |
| JP | 2008-191170 A | 8/2008 |
| JP | 2009-136396 A | 6/2009 |
| JP | 2010-042153 A | 2/2010 |
| JP | 2010-117306 A | 5/2010 |
| JP | 2013-000583 A | 1/2013 |
| WO | 2003/087790 A1 | 10/2003 |
| WO | 2005/047813 A1 | 5/2005 |

* cited by examiner

SPECKLE IMAGING DEVICE, SPECKLE IMAGING SYSTEM, AND SPECKLE IMAGING METHOD

CROSS REFERENCE TO RELATED APPLICATIONS

This application is a U.S. National Phase of International Patent Application No. PCT/JP2016/050910 filed on Jan. 14, 2016, which claims priority benefit of Japanese Patent Application No. JP 2015-029951 filed in the Japan Patent Office on Feb. 18, 2015. Each of the above-referenced applications is hereby incorporated herein by reference in its entirety.

TECHNICAL FIELD

The present technology relates to a speckle imaging device. In particular, the present technology relates to a speckle imaging device, a speckle imaging system, and a speckle imaging method for utilizing speckles generated by irradiation of light to an imaging object.

BACKGROUND ART

Generally, a method for acquiring an X-ray image by injecting a contrast medium into a blood vessel is used for confirming the state and position of the blood vessel in a body. In addition, in recent years, an angiography method for obtaining a tertiary image has also been developed. Examples of the angiography method include computed tomography (CT) angiography and magnetic resonance angiography (MRA).

In addition, a method for capturing a channel such as a blood vessel using an optical technique has also been conventionally proposed (refer to Patent Document 1). In an imaging system described in Patent Document 1, an interference light image is captured at a first timing using interference light which is light emitted from a light emission unit and reflected by an object, and a light emission image of light emitted from the object is captured at a second timing. Furthermore, a method for improving positional accuracy of a blood vessel using an image process has also been proposed (refer to Patent Document 2).

As described above, in recent years, various methods with the use of optical techniques have been developed in the medical field and the like, and detection accuracy thereof has also been increasing year by year. For example, Patent Document 3 discloses a technology for improving signal detection accuracy by having an optical means for generating a plurality of beams in a laser doppler perfusion imaging device including a laser light source, an image detector, and a signal detector.

Incidentally, in relation to the imaging technologies with the use of optical techniques, a reduction in the detection accuracy caused by occurrence of various noises is a matter of concern, and speckle interference is known as one of the noises. The speckle interference is a phenomenon in which a spotty swaying pattern appears on an irradiated surface in accordance with an uneven shape of the irradiated surface.

A technology for suppressing the speckle noise has also been developed. For example, Patent Document 4 discloses an illumination technology, that is, an illumination device that obtains illumination light by mixing light in a first wavelength band and light in a second wavelength band. Specifically, a light source that emits the light in the first wavelength band is a broad area type semiconductor laser, and the illumination device includes a high-frequency wave superimposing means for superimposing a high-frequency signal on a driving current that is supplied to the semiconductor laser, and causing the semiconductor laser to perform multimode oscillation, whereby illumination light without a speckle interference noise can be stably obtained.

In addition, Patent Document 5 discloses a technology for reducing the influence of the speckle noise on obtained image information by forming a light guide using a fiber bundle that is a bunch of a plurality of optical fibers having an optical path length difference equal to or greater than the coherence length of excitation light, and by providing a noise reduction device including the fiber bundle.

CITATION LIST

Patent Document

Patent Document 1: Japanese Patent Application Laid-Open No. 2009-136396
Patent Document 2: Japanese Patent Application Laid-Open No. 2013-583
Patent Document 3: Japanese Patent Application Laid-Open (Translation of PCT Application) No. 2005-515818
Patent Document 4: Japanese Patent Application Laid-Open No. 2010-42153
Patent Document 5: Japanese Patent Application Laid-Open No. 2008-43493

SUMMARY OF THE INVENTION

Problems to be Solved by the Invention

Although various technologies have been developed as the imaging technologies with the use of optical techniques, since the technology of Patent Document 3 is the laser doppler device for observing the frequency shift, it has the following problem: the operation of the laser doppler device is slow, a special skill is required to use the laser doppler device, and the interpretation of the obtained result is not necessarily objective.

In addition, although the technologies of Patent Documents 4 and 5 can suppress the speckle noise, these technologies cannot be applied to a technology for performing imaging by advantageously utilizing the speckle interference.

Therefore, the main object of the present technology is to provide a highly accurate imaging technology that utilizes the speckle interference.

Solutions to Problems

As a result of the intensive study to achieve the above-mentioned object, the inventors of the present application have succeeded in improving the accuracy and completed the present invention by focusing on the advantageous utilization of speckles which have been regarded as noise in the field of imaging technology, and by using a plurality of speckles caused under different irradiation conditions.

Specifically, first, the present technology provides a speckle imaging device including: an irradiation condition setting unit that sets an irradiation condition for coherent light with which an imaging object is irradiated; an imaging unit that captures scattered light obtained from the imaging object irradiated with the coherent light; an image generation unit that generates a speckle-enhanced image from a captured image captured by the imaging unit; and a leveling processing unit that generates a leveled speckle image from speckle-enhanced images corresponding to two or more different irradiation conditions.

The speckle-enhanced image generated by the image generation unit of the speckle imaging device according to the present invention can be an image mapped with a speckle contrast.

The irradiation condition that can be set by the irradiation condition setting unit of the speckle imaging device according to the present invention can be an irradiation angle and/or an irradiation position.

The speckle imaging device according to the present invention can further include an analysis unit that analyzes a state of the imaging object on the basis of the leveled speckle image.

The imaging object for the speckle imaging device according to the present invention may include fluid.

In this case, the analysis unit can analyze a flow velocity of the fluid.

The fluid can be blood, for example.

The speckle imaging device according to the present invention can further include a light source unit that emits coherent light.

Second, the present invention provides a speckle imaging system including at least: an irradiation condition setting unit that sets an irradiation condition for coherent light with which an imaging object is irradiated; an imaging unit that captures scattered light obtained from the imaging object irradiated with the coherent light; an image generation unit that generates a speckle-enhanced image from a captured image captured by the imaging apparatus; and a leveling processing unit that generates a leveled speckle image from speckle-enhanced images corresponding to two or more different irradiation conditions.

The speckle imaging system according to the present invention can further include an analysis unit that analyzes a state of the imaging object on the basis of the leveled speckle image.

Furthermore, a light source that emits coherent light can further be included.

Furthermore, the present invention provides a speckle imaging method for performing: an irradiation condition setting step of setting an irradiation condition for coherent light with which an imaging object is irradiated; an imaging step of capturing scattered light obtained from the imaging object irradiated with the coherent light; an image generation step of generating a speckle-enhanced image from a captured image captured in the imaging step; and a leveling processing step of generating a leveled speckle image from speckle-enhanced images corresponding to two or more different irradiation conditions.

The speckle imaging method according to the present invention can further include an analysis step of analyzing a state of the imaging object on the basis of the leveled speckle image.

Effects of the Invention

According to the present technology, a highly accurate imaging technology that utilizes the speckle interference can be provided.

Note that the effects described herein are not necessarily limited, and any of the effects described in the present technology may be obtained.

MODE FOR CARRYING OUT THE INVENTION

Figure 1:
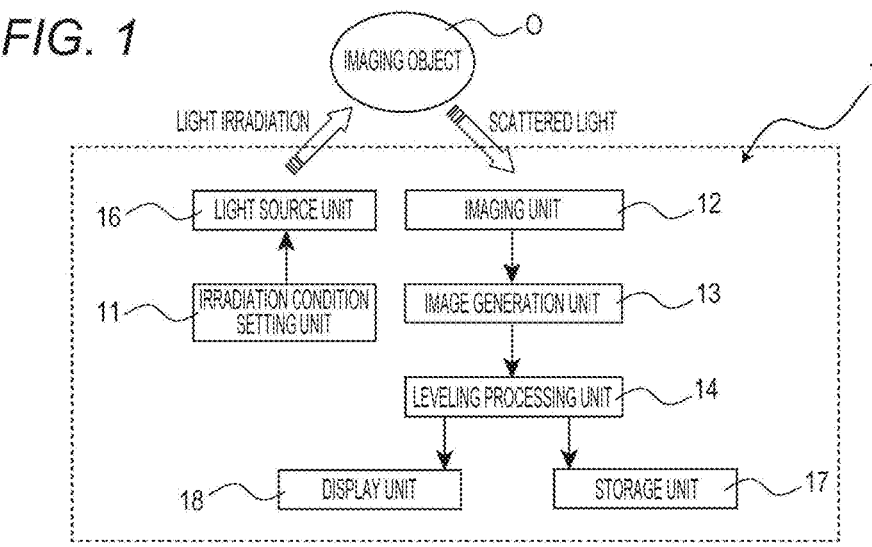
FIG. 1 is a schematic conceptual diagram schematically illustrating a first embodiment of a speckle imaging device 1 according to the present technology.

Hereinafter, preferred embodiments for implementing the present technology will be described with reference to the drawings. The following embodiments indicate examples of representative embodiments of the present technology, and the scope of the present technology is not narrowly interpreted due to these embodiments. Note that the description will be provided in the following order:

1. Speckle imaging device 1
 (1) Irradiation condition setting unit 11
 (2) Imaging unit 12
 (3) Image generation unit 13
 (4) Leveling processing unit 14
 (5) Analysis unit 15
 (6) Light source unit 16
 (7) Storage unit 17
 (8) Display unit 18
 (9) Imaging object O
 (10) Exemplary flow of speckle imaging
 (11) Exemplary endoscope incorporating the speckle imaging device
2. Speckle imaging system 10
3. Speckle imaging method
<1. Speckle Imaging Device 1>

FIG. 1 is a schematic conceptual diagram schematically illustrating a first embodiment of a speckle imaging device 1. The speckle imaging device 1 according to the present technology roughly includes an irradiation condition setting unit 11, an imaging unit 12, an image generation unit 13, and a leveling processing unit 14. In addition, an analysis unit 15, a light source unit 16, a storage unit 17, a display unit 18, and the like can further be included as necessary. Each component will be described in detail below.

(1) Irradiation Condition Setting Unit 11

In the irradiation condition setting unit 11, an irradiation condition for coherent light with which an imaging object O is irradiated is set. The irradiation condition to be set by the irradiation condition setting unit 11 is not particularly limited as long as the effect of the present technology is not impaired. For example, an irradiation angle to the imaging object O, an irradiation position on the imaging object O or the like, or a combination thereof can be set.

The irradiation condition set by the irradiation condition setting unit 11 is transmitted to a light irradiation condition changing mechanism 162 in the light source unit 16 which will be described later, and the light source unit 16 irradiates the imaging object O with light under the set irradiation condition. The specific structure of the light irradiation condition changing mechanism 162 is not particularly limited as long as the effect of the present technology is not impaired, and one or more types of known devices or instruments capable of changing the light irradiation condition can be selected and freely combined. For example, a beam scanning means such as an acousto-optical device (AOD), a piezoelectric device, an electro-optical device, a MEMS mirror, and a galvano mirror, or adaptive optics such as a variable curvature mirror can be used.

In addition, for example, a collimating optical system instrument including a fiber bundle or the like can be used. More specifically, the irradiation condition can be set by selecting one or more fibers in the incident end of the fiber bundle in accordance with the irradiation condition, and introducing coherent light into the selected fiber. As a method of introducing the coherent light into the selected fiber, for example, the beam scanning means or the adaptive optics can be used. Alternatively, the coherent light can be introduced into the target fiber by moving the collimating optical system instrument including the fiber bundle or the like. In addition, the coherent light can be introduced into the target fiber using an optical switch such as an optical type multiplexer (optical add/drop multiplexer) used in an optical communication network such as a planar lightwave circuit.

(2) Imaging Unit 12

In the imaging unit 12, scattered light obtained from the imaging object O irradiated with the coherent light is captured.

An imaging method to be implemented by the imaging unit 12 is not particularly limited as long as the effect of the present technology is not impaired, and one or more types of known imaging methods can be selected and freely combined for use. For example, an imaging method using an image sensor such as a charge coupled device (CCD) sensor and a complementary metal oxide semiconductor (CMOS) sensor can be employed.

(3) Image Generation Unit 13

In the image generation unit 13, a speckle-enhanced image is generated from a captured image captured by the imaging unit 12. Since the speckle imaging device 1 according to the present technology is a technology for advantageously utilizing speckles which have conventionally been processed as noise, an image with enhanced speckles is generated in the image generation unit 13.

The speckle-enhanced image generated by the image generation unit 13 may be any image as long as imaging of interest can be performed. For example, the image generation unit 13 can generate an image mapped with a speckle contrast. In this case, the speckle contrast at the i-th pixel can be expressed by the following mathematical formula (1).

[Mathematical Formula 1]

$$\text{Speckle contrast at } i\text{-th pixel} = \frac{\text{Standard deviation of intensities at } i\text{-th and surrounding pixel}}{\text{Average of intensities at } i\text{-th and surrounding pixels}} \quad (1)$$

Figure 2:
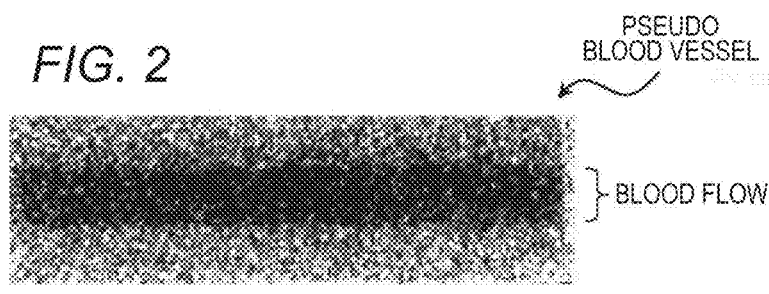
FIG. 2 is a drawing substitute photograph illustrating an exemplary image mapped with a speckle contrast and generated by an image generation unit 13 from a captured image of a pseudo blood vessel with pseudo blood flow captured by the imaging unit 13.

For example, FIG. 2 is an exemplary image mapped with the speckle contrast and generated by the image generation unit 13 from a captured image of a pseudo blood vessel with pseudo blood flow captured by the imaging unit 13. As illustrated in the exemplary image of FIG. 2, a large number of speckles are observed in the part where blood does not flow (part without blood flow), and speckles are hardly observed in the part where blood flows.

(4) Leveling Processing Unit 14

In the leveling processing unit 14, a leveled speckle image is generated from speckle-enhanced images corresponding to two or more different irradiation conditions.

As illustrated in FIG. 2, since the speckles are enhanced in the speckle-enhanced image generated by the image generation unit 13, a boundary between the part where the speckles are generated and the part where no speckles are generated can be observed, but the speckle part is observed as an uneven image. In this regard, the present technology has succeeded in reducing the unevenness from the image of the speckle part by leveling speckle-enhanced images corresponding to two or more different irradiation conditions.

A leveling processing method to be implemented by the leveling processing unit 14 is not particularly limited as long as the effect of the present technology is not impaired, and one or more types of known leveling processing methods can be selected and freely combined for use. Examples of the leveling processing method include a method of leveling speckle-enhanced images corresponding to two or more different irradiation conditions through an averaging process, a method of leveling speckle-enhanced images corresponding to two or more different irradiation conditions through an integration process, and the like.

Figure 3:
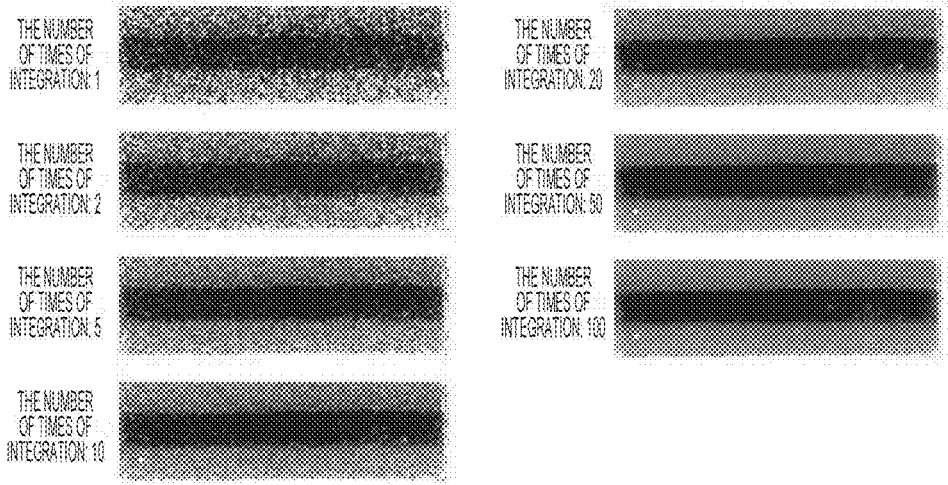
FIG. 3 is drawing substitute photographs illustrating exemplary leveled speckle images generated from speckle-enhanced images corresponding to two or more different irradiation conditions with respect to the pseudo blood vessel with the pseudo blood flow.
Figure 4:
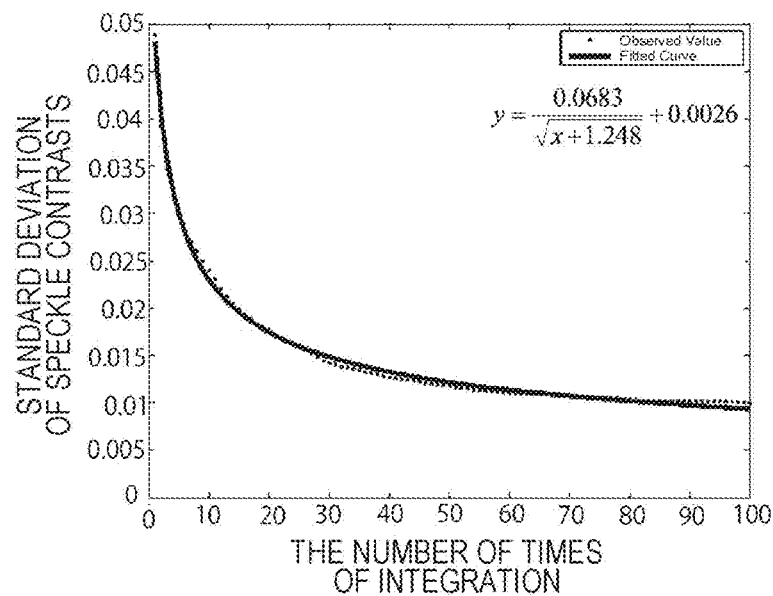
FIG. 4 is a drawing substitute graph illustrating the relation between the number of times of integration of speckle contrasts corresponding to two or more different irradiation conditions and standard deviation of speckle contrasts.

FIG. 3 is exemplary leveled speckle images generated from speckle-enhanced images corresponding to two or more different irradiation conditions with respect to the pseudo blood vessel with the pseudo blood flow. The examples illustrated in FIG. 3 are exemplary images obtained by leveling speckle-enhanced images corresponding to two or more different irradiation conditions through the integration process. The respective images indicate exemplary leveled speckle images for a case where the number of times of integration is 1 (no leveling process) and the number of times of integration is 2, 5, 20, 50, and 100. In addition, FIG. 4 is a drawing substitute graph illustrating the relation between the number of times of integration of speckle contrasts corresponding to two or more different irradiation conditions and standard deviation of speckle contrasts.

As illustrated in FIG. 3, as the number of times of integration increases, the unevenness is removed from the image of the speckle part, and a more easily observable image can be obtained.

(5) Analysis Unit 15

Figure 5:
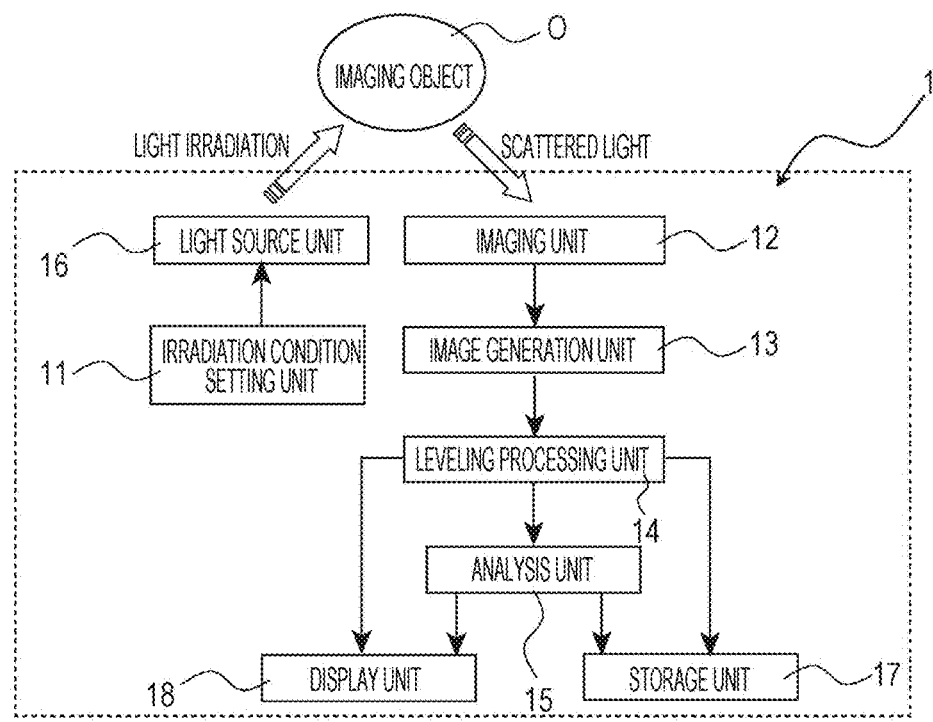
FIG. 5 is a schematic conceptual diagram schematically illustrating a second embodiment of the speckle imaging device 1 according to the present technology.

FIG. 5 is a schematic conceptual diagram schematically illustrating a second embodiment of the speckle imaging device 1 according to the present technology. The speckle imaging device 1 according to the second embodiment illustrated in FIG. 5 includes the analysis unit 15.

In the analysis unit 15, the state of the imaging object O is analyzed on the basis of the leveled speckle image leveled by the leveling processing unit 14. The analysis unit 15 is not indispensable to the speckle imaging device 1 according to the present technology, and the state of the imaging object O can be analyzed on the basis of the leveled speckle image leveled by the leveling processing unit 14 using an external analysis device or the like.

For example, the position of the blood vessel, the blood flow velocity, and the like can be analyzed from the exemplary leveled images illustrated in FIG. 3.

(6) Light Source Unit 16

The speckle imaging device 1 according to the present technology can further include the light source unit 16 that emits coherent light. The light source unit 16 is not indispensable to the speckle imaging device 1 according to the present technology, and the imaging object O can be irradiated with light using an external light source, for example.

The coherent light emitted from the light source unit 16 means that the phase relation between lightwaves at any two points in a light flux is invariable and constant in terms of time, and even after the light flux is split using any method, and a large optical path difference is provided, the recombined light flux exhibits perfect coherence.

The type of coherent light to be emitted from the light source unit 16 is not particularly limited as long as the effect of the present technology is not impaired. Examples of the coherent light can include laser light, LED light, and the like. As the light source unit 16 that emits laser light, for example, one or more types of lasers such as an argon ion (Ar) laser, a helium-neon (He—Ne) laser, a dye laser, a krypton (Cr) laser, a semiconductor laser, or a solid-state laser which is a combination of a semiconductor laser and a wavelength conversion optical device can be freely combined for use.

The light source unit 16 roughly includes a light irradiation mechanism 161 and the light irradiation condition changing mechanism 162. Since the specific configuration of the light irradiation condition changing mechanism 162 is as described above, the description thereof is omitted here.

(7) Storage Unit 17

The speckle imaging device 1 according to the present technology can further include the storage unit 17 that stores the leveled speckle image generated by the leveling processing unit 14 and the analysis result provided by the analysis unit 15. The storage unit 17 is not indispensable to the speckle imaging device 1 according to the present technique, and, for example, an external storage device can be connected to store the leveled speckle image and the analysis result.

In the speckle imaging device 1 according to the present technology, the storage unit 17 may be provided separately for each of the leveling processing unit 14 and the analysis unit 15, or the single storage unit 17 can be designed to store the leveled speckle image generated and the analysis result provided by the analysis unit 15.

(8) Display Unit 18

The speckle imaging device 1 according to the present technology can further include the display unit 18 that displays the leveled speckle image generated by the leveling processing unit 14 and the analysis result provided by the analysis unit 15. The display unit 18 is not indispensable to the speckle imaging device 1 according to the present technology, and the imaging object O can be irradiated with light using, for example, an external monitor or the like.

In the speckle imaging device 1 according to the present technology, the display unit 18 may be provided separately for each of the leveling processing unit 14 and the analysis unit 15, or the single display unit 18 can be designed to display the leveled speckle image generated and the analysis result provided by the analysis unit 15.

(9) Imaging Object O

The speckle imaging device 1 according to the present technology can be intended for various objects, and it can be suitably used for imaging an object including fluid, for example. Due to the property of speckles, fluid has the property of hardly generating speckles. Therefore, an object including fluid is imaged using the speckle imaging device 1 according to the present technology, whereby a boundary between the fluid and the other part, the flow velocity of the fluid, and the like can be obtained.

More specifically, the imaging object O can be a living body, and the fluid can be blood. For example, if the speckle imaging device 1 according to the present technology is mounted on a surgical microscope, a surgical endoscope or the like, surgery can be performed while the position of a blood vessel is confirmed. Therefore, it is possible to perform more safe and accurate surgery, and contribute to the further development of the medical technology.

(10) Exemplary Flow of Speckle Imaging

Figure 6:
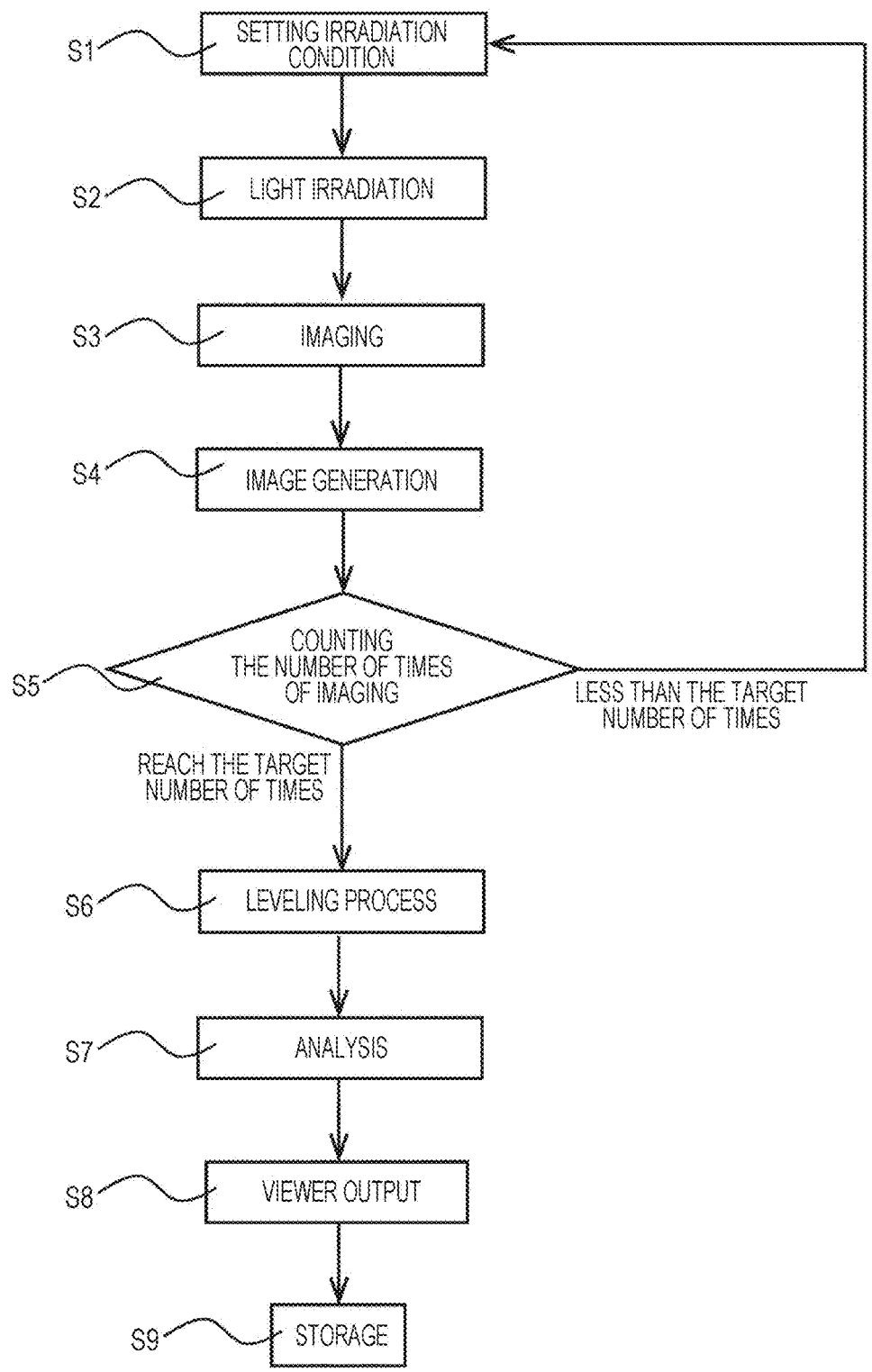
FIG. 6 is a flowchart illustrating exemplary speckle imaging that is performed using the speckle imaging device 1 according to the present technology.

FIG. 6 is a flowchart illustrating exemplary speckle imaging that is performed using the speckle imaging device 1 according to the present technology. Hereinafter, an exemplary flow will be described in time-series order.

(a) Setting Irradiation Condition (S1)

First, an irradiation condition is set by the irradiation condition setting unit 11.

(b) Light Irradiation (S2)

Next, in accordance with the irradiation condition set by the irradiation condition setting unit 11, the imaging object O is irradiated with coherent light.

(c) Imaging (S3)

Next, scattered light obtained from the illuminated object irradiated with the light is captured by the imaging unit 12.

(d) Image Generation (S4)

A speckle-enhanced image is generated by the image generation unit 13 from the captured image.

(e) Counting the Number of Times of Imaging (S5)

The number of times that the imaging has been performed by the imaging unit 12 is counted. In a case where the target number of times has not been reached, the process returns to (a) Setting irradiation condition (S1), where an irradiation condition different from the previous irradiation condition is set. Then, (b) Light irradiation (S2), (c) Imaging (S3), and (d) Image generation (S4) are repeated in this order in a similar manner.

In a case where the number of times of imaging has reached the target number of times, the process advances to (f) Leveling process (S6) below.

(f) Leveling Process (S6)

A leveled speckle image is generated by the leveling processing unit 14 from a plurality of speckle-enhanced images generated so that the number of speckle-enhanced images is equal to the target number of times.

(g) Analysis (S7)

In a case where the analysis unit 15 is provided in the speckle imaging device 1 according to the present technology, the state analysis is performed after the leveling process (S6).

(h) Viewer Output (S8)

The leveled speckle image generated by the leveling processing unit 14 and the analysis result obtained through the state analysis (S7) are output to a viewer.

(i) Storage (S9)

Then, the leveled speckle image generated by the leveling processing unit 14 and the analysis result obtained through the state analysis (S7) are stored, whereby the sequential flow is finished.

(11) Exemplary Endoscope Incorporating the Speckle Imaging Device

Figure 7:
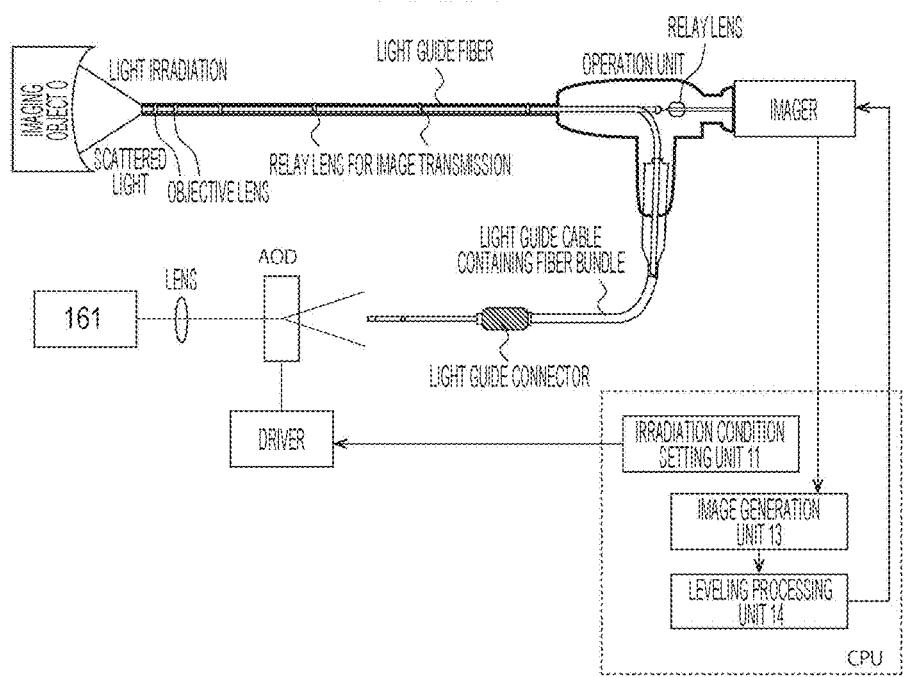
FIG. 7 is a schematic conceptual diagram schematically illustrating an exemplary endoscope incorporating the speckle imaging device 1 according to the present technology.

FIG. 7 is a schematic conceptual diagram schematically illustrating an exemplary endoscope incorporating the speckle imaging device 1 according to the present technology.

In the example illustrated in FIG. 7, light from the light irradiation mechanism 161 is collimated by a collimating optical system (such as a lens), deflected by an acousto-optical device (AOD) operated by a driver, and connected to a light guide connector. The light from the collimating optical system passes through the light guide connector and is collected within the core diameter of one fiber in the incident end of the fiber bundle in the light guide cable. The incident light passes through the endoscope and is radiated to the imaging object O (for example, a living body) in a viewing angle direction through an objective lens.

In this case, the deflection angle is changed by changing an input RF frequency to the AOD, whereby the incident fiber in the fiber bundle can be changed. Consequently, the emission angle and position of the illumination light emitted from the objective lens can be actively changed. More specifically, a timing trigger is input to the AOD by the irradiation condition setting unit 11, and a timing trigger to an imager is input after an appropriate delay time. After one frame is photographed, a timing trigger is input to the AOD again by the irradiation condition setting unit 11 so that light is introduced to another fiber position. This operation is successively repeated, whereby image data at each fiber position can be acquired. On this occasion, two-dimensional scanning is also enabled by arranging AODs in two directions orthogonal to a deflection direction.

Scattered light obtained from the imaging object O irradiated with the light is acquired as an image by the imager via a relay lens, a speckle-enhanced image is generated by the image generation unit 13 in the CPU, and speckle-enhanced images corresponding to two or more different irradiation conditions are leveled by the leveling processing unit 14. Consequently, the speckle contrast or its spatial image is displayed, whereby observation of a deep part in the vicinity of epidermis such as intravascular blood flow in the living body (imaging object O) is enabled, and the blood flow velocity thereof can be grasped.

<2. Speckle Imaging System 10>

Figure 8:
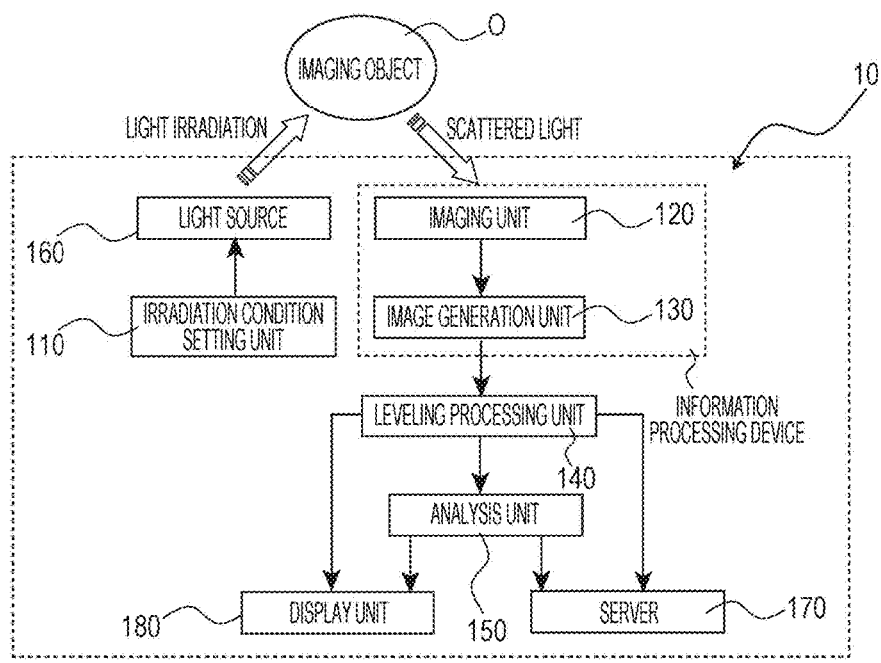
FIG. 8 is a schematic conceptual diagram schematically illustrating a speckle imaging system 10 according to the present technology.

FIG. 8 is a schematic conceptual diagram schematically illustrating a speckle imaging system 10 according to the present technology. The speckle imaging device 1 according to the present technology roughly includes an irradiation condition setting unit 110, an imaging unit 120, an image generation unit 130, and a leveling processing unit 140. In addition, an analysis unit 150, a light source 160, a server 170, a display unit 180, and the like can further be included as necessary. Note that since the irradiation condition setting unit 110, the imaging unit 120, the image generation unit 130, the leveling processing unit 140, the analysis unit 150, the light source 160, the server 170, and the display unit 180 are respectively the same as the irradiation condition setting unit 11, the imaging unit 12, the image generation unit 13, the leveling processing unit 14, the analysis unit 15, the light source unit 16, the storage unit 17, and the display unit 18 of the speckle imaging device 1 according to the present technology described above, the descriptions thereof are omitted here.

In the speckle imaging system 10 according to the present technology, each component may exist as an independent device, or a plurality of components may exist as a single device as can be seen, for example, in an information processing device including the image generation unit 130 and the leveling processing unit 140 illustrated in FIG. 8. In addition, a part or all of the components or devices can be connected via a network.

<3. Speckle Imaging Method>

Figure 9:
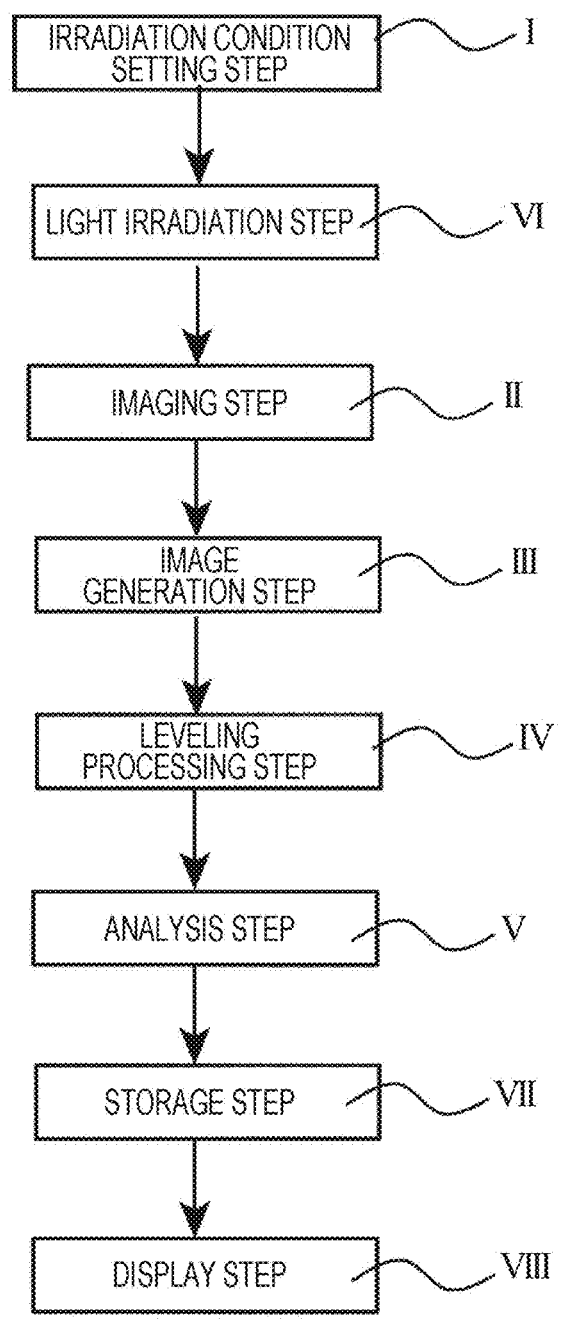
FIG. 9 is a process chart for a speckle imaging method according to the present technology.

FIG. 9 is a process chart for a speckle imaging method according to the present technology. The speckle imaging method according to the present technology is a method of performing steps roughly including irradiation condition setting step I, imaging step II, image generation step III, and leveling processing step IV. In addition, analysis step V, light irradiation step VI, storage step VII, display step VIII, and the like can further be performed as necessary.

Note that since irradiation condition setting step I, imaging step II, image generation step III, leveling processing step IV, analysis step V, light irradiation step VI, storage step VII, and display step VIII are the same as the respective procedures that are performed by the irradiation condition setting unit 11, the imaging unit 12, the image generation unit 13, the leveling processing unit 14, the analysis unit 15, the light source unit 16, the storage unit 17, and the display unit 18 of the speckle imaging device 1 according to the present technology described above, the descriptions thereof are omitted here.

Note that although storage step VII is performed after analysis step V and before display step VIII in the description of FIG. 9, the processing order is not limited to this example. In a case where the leveled speckle image generated in leveling processing step IV is stored, storage step VII can be performed after leveling processing step IV. In addition, in a case where all the items such as the condition set in irradiation condition setting step I, the image captured in imaging step II, and the image generated in image generation step III are also stored, storage step VII can be repeated after each of these steps.

Moreover, although display step VIII is performed after storage step VII in the description of FIG. 9, the processing order is not limited to this example. In a case where the leveled speckle image generated in leveling processing step IV is displayed, display step VIII can be performed after leveling processing step IV. In addition, in a case where all the items such as the condition set in irradiation condition setting step I, the image captured in imaging step II, and the image generated in image generation step III are also displayed, display step VIII can be repeated after each of these steps.

Note that the present technology can also be configured as follows.

(1) A speckle imaging device including:
an irradiation condition setting unit that sets an irradiation condition for coherent light with which an imaging object is irradiated;
an imaging unit that captures scattered light obtained from the imaging object irradiated with the coherent light;
an image generation unit that generates a speckle-enhanced image from a captured image captured by the imaging unit; and
a leveling processing unit that generates a leveled speckle image from speckle-enhanced images corresponding to two or more different irradiation conditions.

(2) The speckle imaging device according to (1), in which the speckle-enhanced image is an image mapped with a speckle contrast.

(3) The speckle imaging device according to (1) or (2), in which the irradiation condition is an irradiation angle and/or an irradiation position.

(4) The speckle imaging device according to any of (1) to (3), further including an analysis unit that analyzes a state of the imaging object on the basis of the leveled speckle image.

(5) The speckle imaging device according to any of (1) to (4), in which the imaging object includes fluid.

(6) The speckle imaging device according to (4), in which the imaging object includes fluid, and a flow velocity of the fluid is analyzed in the analysis unit.

(7) The speckle imaging device according to (5), in which the fluid is blood.

(8) The speckle imaging device according to any of (1) to (7), further including a light source unit that emits coherent light.

(9) A speckle imaging system including at least:
an irradiation condition setting unit that sets an irradiation condition for coherent light with which an imaging object is irradiated;
an imaging unit that captures scattered light obtained from the imaging object irradiated with the coherent light;
an image generation unit that generates a speckle-enhanced image from a captured image captured by the imaging apparatus; and
a leveling processing unit that generates a leveled speckle image from speckle-enhanced images corresponding to two or more different irradiation conditions.

(10) The speckle imaging system according to (9), further including an analysis unit that analyzes a state of the imaging object on the basis of the leveled speckle image.

(11) The speckle imaging system according to (9) or (10), further including a light source that emits coherent light.

(12) A speckle imaging method for performing:
an irradiation condition setting step of setting an irradiation condition for coherent light with which an imaging object is irradiated;
an imaging step of capturing scattered light obtained from the imaging object irradiated with the coherent light;
an image generation step of generating a speckle-enhanced image from a captured image captured in the imaging step; and
a leveling processing step of generating a leveled speckle image from speckle-enhanced images corresponding to two or more different irradiation conditions.

(13) The speckle imaging method according to (12), for further performing an analysis step of analyzing a state of the imaging object on the basis of the leveled speckle image.

REFERENCE SIGNS LIST

1 Speckle imaging device
11 Irradiation condition setting unit
12 Imaging unit
13 Image generation unit
14 Leveling processing unit
15 Analysis unit
16 Light source unit
17 Storage unit
18 Display unit
O Imaging object
10 Speckle imaging system
110 Irradiation condition setting unit
120 Imaging unit
130 Image generation unit
140 Leveling processing unit
150 Analysis unit
160 Light source
170 Server
180 Display unit
I Irradiation condition setting step
II Imaging step
III Image generation step
IV Leveling processing step
V Analysis step
VI Light irradiation step
VII Storage step
VIII Display step

The invention claimed is:

1. A speckle imaging device comprising:
an irradiation condition setting unit that sets an irradiation condition for coherent light with which an imaging object is irradiated;
an imaging unit that captures scattered light obtained from the imaging object irradiated with the coherent light;
an image generation unit that generates a speckle-enhanced image from a captured image captured by the imaging unit; and
a leveling processing unit that generates a leveled speckle image from speckle-enhanced images corresponding to two or more different irradiation conditions.

2. The speckle imaging device according to claim 1, wherein
the speckle-enhanced image is an image mapped with a speckle contrast.

3. The speckle imaging device according to claim 1, wherein
the irradiation condition is an irradiation angle and/or an irradiation position.

4. The speckle imaging device according to claim 1, further comprising an analysis unit that analyzes a state of the imaging object on the basis of the leveled speckle image.

5. The speckle imaging device according to claim 1, wherein
the imaging object includes fluid.

6. The speckle imaging device according to claim 4, wherein
the imaging object includes fluid, and
a flow velocity of the fluid is analyzed in the analysis unit.

7. The speckle imaging device according to claim 5, wherein
the fluid is blood.

8. The speckle imaging device according to claim 1, further comprising a light source unit that emits coherent light.

9. A speckle imaging system comprising at least:
an irradiation condition setting unit that sets an irradiation condition for coherent light with which an imaging object is irradiated;
an imaging unit that captures scattered light obtained from the imaging object irradiated with the coherent light;
an image generation unit that generates a speckle-enhanced image from a captured image captured by the imaging unit; and
a leveling processing unit that generates a leveled speckle image from speckle-enhanced images corresponding to two or more different irradiation conditions.

10. The speckle imaging system according to claim 9, further comprising an analysis unit that analyzes a state of the imaging object on the basis of the leveled speckle image.

11. The speckle imaging system according to claim 9, further comprising a light source that emits coherent light.

12. A speckle imaging method for performing:
- an irradiation condition setting step of setting an irradiation condition for coherent light with which an imaging object is irradiated;
- an imaging step of capturing scattered light obtained from the imaging object irradiated with the coherent light;
- an image generation step of generating a speckle-enhanced image from a captured image captured in the imaging step; and
- a leveling processing step of generating a leveled speckle image from speckle-enhanced images corresponding to two or more different irradiation conditions.

13. The speckle imaging method according to claim 12, for further performing an analysis step of analyzing a state of the imaging object on the basis of the leveled speckle image.

\* \* \* \* \*